United States Patent [19]

Fujioka et al.

[11] Patent Number: 5,451,217
[45] Date of Patent: Sep. 19, 1995

[54] DISPOSABLE DIAPERS

[75] Inventors: Yoshihisa Fujioka, Kagawa; Hirotomo Mukai, Kawanoe, both of Japan

[73] Assignee: Uni-Charm Corporation, Ehime, Japan

[21] Appl. No.: 103,687

[22] Filed: Aug. 10, 1993

[30] Foreign Application Priority Data

Aug. 25, 1992 [JP] Japan ................... 4-225945

[51] Int. Cl.6 ........................ A61F 13/15; A61F 13/20
[52] U.S. Cl. ..................................... 604/378; 604/358; 604/385.1; 604/393
[58] Field of Search ............ 604/358, 385.1, 393–395, 604/382, 383, 378

[56] References Cited

U.S. PATENT DOCUMENTS

| | | |
|---|---|---|
| 3,225,918 | 12/1965 | Keine . |
| 3,881,489 | 5/1975 | Hartwell ........................... 604/369 |
| 4,205,679 | 6/1980 | Repke et al. ..................... 604/369 |
| 4,427,408 | 1/1984 | Karami . |
| 4,648,876 | 3/1987 | Becker et al. . |
| 4,713,068 | 12/1987 | Wang et al. . |
| 4,758,239 | 7/1988 | Yeo et al. . |
| 4,818,600 | 4/1989 | Braun et al. . |
| 4,959,059 | 9/1990 | Eilender et al. ................... 604/358 |
| 5,137,525 | 8/1992 | Glassman . |
| 5,207,663 | 5/1993 | McQueen ........................... 604/358 |
| 5,236,430 | 8/1993 | Bridges ............................... 604/358 |

FOREIGN PATENT DOCUMENTS

| | | |
|---|---|---|
| 0422504 | 4/1991 | European Pat. Off. . |
| 2517525 | 6/1983 | France . |
| 2169789 | 7/1986 | United Kingdom ............... 604/358 |
| 2236663 | 4/1991 | United Kingdom ............... 604/358 |
| 2257347 | 1/1993 | United Kingdom ............... 604/358 |
| 2257347 | 1/1993 | United Kingdom . |

*Primary Examiner*—Randall L. Green
*Assistant Examiner*—P. Zuttarelli
*Attorney, Agent, or Firm*—Lowe, Price, LeBlanc & Becker

[57] ABSTRACT

A disposable diaper comprising front and rear bodies separately formed and welded together along only respective lower ends of a crotch zone, and a breathability of said front body being different from that of said rear body.

7 Claims, 1 Drawing Sheet

DISPOSABLE DIAPERS

BACKGROUND OF THE INVENTION

The present invention relates to disposable diapers.

Conventionally, the typical disposable diapers employ moisture-permeable but liquid-impermeable film, for example, resinous film mixed with inorganic fine particles as a backsheet in order to eliminate or alleviate unpleasant stuffiness often experienced by diaper wearers.

Such backsheet has a moisture permeability in the order of 1500 to 3000 $g/m^2 24hs$ (ASTM E96-66) and a water pressure resistance of 1000 $cmH_2O$ or higher (JIS L 1092). These values have been found to be sufficient for urine-impermeability but insufficient for a desired moisture-permeability. Therefore, the stuffiness generated within the diaper can not be suppressed or alleviated by such a backsheet to the desired level where the wearers are not given any discomfort and are substantially free from any adverse effect of stuffiness that would possibly cause a skin disease. The higher the moisture-permeability of the backsheet, the lower the liquid-impermeability thereof should be, resulting in leakage of liquid excretion. Confronting such an antinomic relationship, the highest priority is usually given to -the liquid-impermeability.

The typical example of the open type disposable diaper having tape fastener means used to fasten front and rear bodies to each other at the level of waist line is disclosed in Japanese Patent No. 1977-40267. This example comprises a liquid-permeable topsheet, a liquid-impermeable backsheet, and a liquid-absorbent panel sandwiched therebetween wherein a pair of side flaps are formed by portions of the top- and backsheets extending outward beyond laterally opposite sides of the panel and the respective side flaps are formed at the crotch level with cutouts destined to define leg-openings around which the respective side flaps are provided with elastic members serving to seal the side flaps around the respective legs of the wearer and wherein the rear body is provided at laterally opposite sides with tape fasteners used to fasten the rear body to the front body.

As the diaper disclosed by the above-identified Japanese Patent No. 1977-40267 is typical, the cutouts formed in opposite sides of the crotch zone for improved fitness of the diaper to the wearer's body necessarily reduce the width of the crotch zone and it is practically impossible for the crotch zone to surround the wearer's thighs. The crotch zone thus width-reduced inevitably decreases the ability of the crotch zone to absorb liquid excretion and to catch solid excretion, so leakage of excretion, particularly liquid excretion, readily occurs along opposite side edges of the crotch zone.

Generally in the well known diaper of the type as disclosed by the above-identified Japanese Patent, a fold line of the crotch zone corresponding to the boundary line of the front and rear bodies extends horizontally and in parallel to the waist line. In addition, the liquid-absorbent panel has so-called semi-rigidity, since it often comprises a more or less compressed accumulation of fluff pulp and tissue paper covering top- and back surfaces of this accumulation. Accordingly, the crotch zone of the diaper is not able to fit the corresponding zone of the wearer's body, thus not only giving the wearer the feeling of incompatibility but also causing said leakage.

SUMMARY OF THE INVENTION

In view of the problem as mentioned above, it is a principal object of the invention to provide a disposable diaper comprising front and rear bodies separately formed and then welded together so as to solve the above mentioned problem.

To achieve the object set forth above, the invention generally resides in a disposable diaper comprising a front body and a rear body separately formed, said front and rear bodies each comprising a liquid-permeable topsheet, a breathable but liquid-impermeable backsheet and a liquid-absorbent panel sandwiched therebetween, said front and rear bodies being welded together only along respective lower ends of the crotch zone, and a breathability of said front body is different from that of said rear body.

Preferably, said front and rear bodies are welded together adjacent lower ends along a welding line convexly curved toward the waist lines of said front and rear bodies so as to define said crotch zone.

Preferably, said front and rear bodies are partially cut away outside said crotch zone defined by said convexly curved welding line.

It should be understood that a backsheet in one of front and rear bodies having a breathability lower than that of the backsheet in the other body may have not a breathability at all within the scope of the invention.

According to the invention constructed as outlined above, ventilation between the diaper and the outside air is achieved through the front body or the rear body including the backsheet having a higher breathability.

With the diaper put on the wearer, the convexly curved welding line is properly positioned on the crotch of the wearer and at least laterally opposite sides of the diaper's crotch zone cover the insides of the wearer's thighs, namely, said crotch zone of the diaper covers substantially the entire crotch of the wearer.

BRIEF DESCRIPTION OF THE DRAWINGS

The invention will be described by way of example in reference with the accompanying drawings, in which.

DESCRIPTION OF THE PREFERRED EMBODIMENTS

Figure 2:
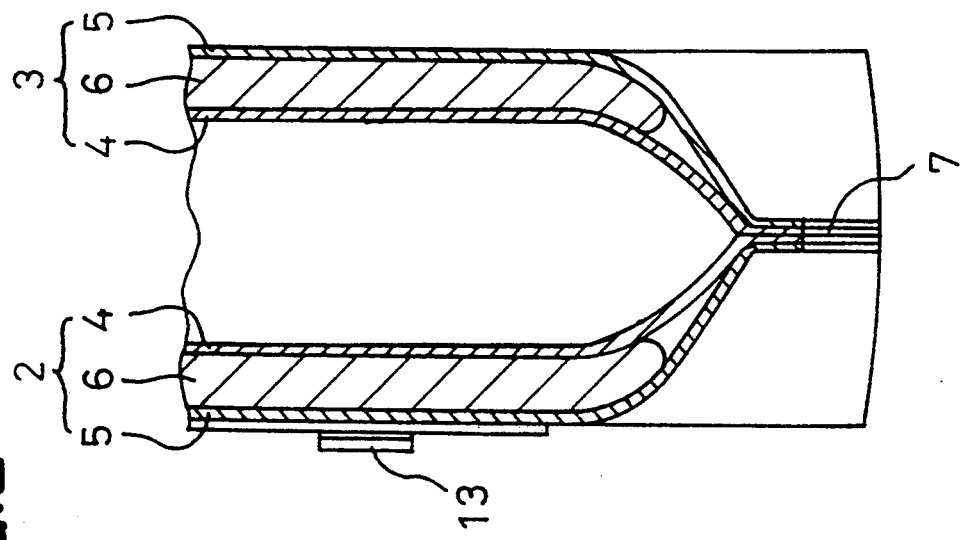
FIG. 2 is a sectional view taken along a line X—X in FIG. 1.
Figure 1:
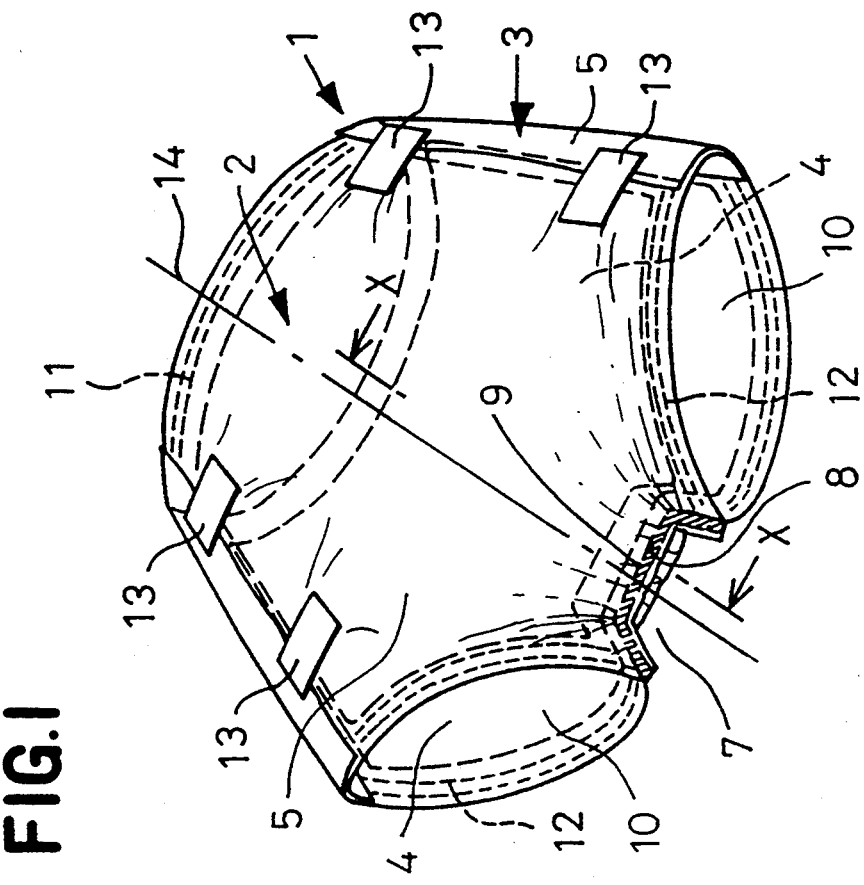
FIG. 1 is a front view showing an embodiment of a disposable diaper constructed according to the teachings of the invention.

Referring to FIGS. 1 and 2, a diaper 1 generally comprises front and rear bodies 2, 3. The rear body 3 is transversely dimensioned to be larger than the front body 2. Each of front and rear bodies 2, 3 comprises a liquid-permeable topsheet 4, a liquid-impermeable backsheet 5 and a liquid-absorbent panel 6 sandwiched between said top- and backsheets 4, 5.

Lower ends of front and rear bodies 2, 3 are formed at the middle positions with cutouts 7 convexly curved toward the waist lines of front and rear bodies 2, 3. The front and rear bodies 2, 3 are welded together along a heat or supersonic welding line 8 extending in parallel with the cutouts 7 so as to leave narrow edges of the cutouts 7 not welded. Sizes, shapes and radiuses of curvature of the welding line 8 may be appropriately selected depending on whether the diaper is for an adult or for a baby so far as the welding line 8 is convexly curved toward the waist lines of the front and rear bodies 2, 3 and at least the inside portions of the respective leg-openings 10 extend downward beyond an apex 9 of the convexly curved welding line 8.

Circumferentially stretchable elastic members 11, 12 are interposed between edges of top- and backsheets 4, 5 extending beyond the panel 6 around waist-opening and leg-openings, respectively, and said edges are closed together by hot melt type adhesive or said welding means. Laterally opposite side edges of top- and backsheets 4, 5 extending beyond the panel 6 are also closed together in the same manner and the rear body 3 is provided on laterally opposite side edges with a plurality of fastener means 13 each comprising a tape fastener applied on one side with pressure-sensitive adhesive, by which the laterally opposite sides of the rear body 3 are fastened to the corresponding sides of the front body 2.

While laterally opposite side edges and lower edges around the respective leg-openings of front and rear bodies 2, 3 are illustrated to extend neither in parallel with nor perpendicularly to a vertical axis 14, these side edges may extend in parallel with the vertical axis 14 and those lower edges around the respective leg-openings may extend perpendicularly to said vertical axis 14 within the scope of the invention.

The diaper 1 opens at the laterally opposite sides, therefore, at the waist-opening as well as the leg-openings also and, after joining with use of the fastener means as illustrated by FIG. 1, the laterally opposite sides are closed and, as a consequence, the waist-opening as well as the leg-openings are also closed. The sizes of these openings depend on the overlap width of the front and rear bodies 2, 3 and the overlap width depends, in turn, on the sizes of individual wearer's waist and legs (thighs). It is also possible to weld the laterally opposite side edges together to obtain a pants type diaper, and in such case no fastener means will be required.

The front body 2 or a rear body 3 uses the backsheet 5 having a breathability of 3 cc/cm$^2$/sec or higher and a water pressure resistance of 50 cm H$_2$O or higher. Which of the front and rear bodies 2, 3 should use a backsheet having such breathability and water pressure resistance depends on, for an example, whether the diaper is for a adult or for baby. In general, adult patients would lie face up and neither body weight nor significant water pressure resistance load would be exerted on the front body of the diaper, so the backsheet having a higher breathability may be used in the front body to minimize or alleviate stuffness possibly generated within the diaper. On the other hand, some babies lie face up and some babies lie face down. For the latter case, a backsheet having a higher breathability may be used in the rear body.

As material of which the backsheet of a higher breathability is made, it is preferred to employ hydrophobic nonwoven fabric of relatively high density, water repellence treated nonwoven fabric, plastic film formed with a plurality of fine pinholes, fine netty meshes or the like.

The other components of diaper may be those commonly used for the diaper as is well known in the art. For example, the topsheet 4 may be made of nonwoven fabric, the backsheet 5 other than said highly breathable backsheet may be made of plastic film, the panel 6 may be made of fluff pulp mixed with superabsorbent polymer, the elastic members 11, 12 may be made of natural or synthetic rubber, and the substrate of the fastener means 18 may be made of fine quality paper or a laminate of nonwoven fabric and plastic film.

The disposable diaper constructed according to the invention as described hereinabove allows undesirable stuffness that has been more or less generated within the diaper to be minimized or alleviated by selectively adjusting the breathability of the front or rear body so as to be higher than that of the other body, depending on the type of final article and simultaneously allows excretion leakage that has often occurred in the conventional diaper to be effectively avoided by said other body having a lower breathability.

According to the invention, the formation of the cutouts in opposite sides of the crotch zone so as to define the leg-openings never results in an unacceptably narrow width of the crotch zone, since the welding line convexly curved toward the waist line allows the width of the crotch zone defined between the opposite side edges of the crotch zone to be dimensioned adequately large. In this manner, the crotch zone covers at least the insides of the respective thighs sufficiently to improve its ability of absorption and thereby prevents excretion from leaking along its edges around the respective thighs. Particularly in the case of an open type diaper, provision of said convexly curved welding line allows the diaper to be properly put on the wearer, since the crotch zone of the diaper well gets to fit the corresponding zone of the wearer's body.

What is claimed is:

1. A disposable diaper comprising a front body and a rear body separately formed, said front and rear bodies each comprising a liquid-permeable topsheet, a breathable but liquid-impermeable backsheet and a liquid-absorbent panel sandwiched therebetween, said front and rear bodies being welded together only along respective lower ends of a crotch zone, and the breathability of said front body is greater than that of said rear body.

2. A disposable diaper according to claim 1, wherein said front and rear bodies are welded together adjacent their lower ends along a welding line convexly curved toward waist line of said front and rear bodies so as to define said crotch zone.

3. A disposable diaper according to claim 1, wherein said front and rear bodies are partially cut away outside said crotch zone defined by said convexly curved welding line.

4. Disposable absorbent pants comprising a front body (2), a rear body (3), said pants having a waist opening, two leg openings (10) and a crotch area extending between said leg openings (10),
(A) each said body (2, 3) comprised of
(a) a liquid-permeable topsheet (4),
(b) a liquid-impermeable backsheet (5), and
(c) a mass of absorbent material (6) sandwiched between said topsheet (4) and said backsheet (5),
(d) the breathability of said backsheet (5) on said front body (2) being different from the breathability of the backsheet (5) on said rear body (3),
(B) each body (2, 3) having spaced apart side edges, each side edge of said front body (2) being detachably joined in over-lapping relationship to a side edge of said rear body (3) by a plurality of fastener means (13), and
(C) each body (2, 3) having bottom edges, portions of the bottom edges of said bodies (2, 3) being spaced apart from each other to form leg openings (10) and the remaining portions of the bottom edges of said bodies (2, 3) being bonded together along a convexly curved welding line (8) to thereby form a convexly curved crotch zone that extends between said leg openings (10), said convexly curved crotch zone having an apex (9) that is closer to said waist opening than are said leg openings (10).

5. Disposable pants according to claim 4 wherein the breathability of said backsheet (5) on said front body (2) is greater than the breathability of said backsheet (5) on said rear body (3).

6. Disposable pants according to claim 4 wherein the breathability of said backsheet (5) on said rear body (3) is greater than the breathability of said backsheet on said front body (2).

7. A disposable diaper comprising a front body and a rear body, said front and rear bodies each comprising a liquid-permeable topsheet, a breathable but liquid-impermeable backsheet and a liquid absorbent panel sandwiched therebetween, wherein the breathability of said front body is greater than that of said rear body.

* * * * *